United States Patent
Velkovska et al.

(10) Patent No.: US 6,471,917 B1
(45) Date of Patent: Oct. 29, 2002

(54) SYSTEM AND METHOD FOR SINGLE OR MULTIPLE BEAD DISTRIBUTION WITH AN ADJUSTABLE CAPILLARY

(75) Inventors: Svetlana Velkovska, San Jose; Kerwin Ng, San Francisco; Haim Kedar, Palo Alto, all of CA (US)

(73) Assignee: Affymax, Inc., Palo Alto, CA (US)

( * ) Notice: Subject to any disclaimer, the term of this patent is extended or adjusted under 35 U.S.C. 154(b) by 0 days.

(21) Appl. No.: 09/547,356

(22) Filed: Apr. 11, 2000

(51) Int. Cl.[7] ............... G01N 1/10; G01N 35/08; G01N 1/18; B01L 3/02; B01L 3/00
(52) U.S. Cl. .............. 422/100; 422/99; 422/67; 422/68.1; 436/54; 436/178; 436/180
(58) Field of Search ............... 422/100, 99, 67, 422/68.1; 436/54, 180, 178

(56) References Cited

U.S. PATENT DOCUMENTS

| | | |
|---|---|---|
| 3,568,735 A | 3/1971 | Lancaster ............... 141/238 |
| 3,598,251 A | 8/1971 | Sieurin |
| 3,932,141 A | 1/1976 | Beall et al. |
| 3,940,172 A | 2/1976 | Hutson et al. |
| 4,101,284 A | 7/1978 | Difiglio et al. |
| 4,266,905 A | 5/1981 | Birk et al. |
| 4,554,839 A | 11/1985 | Hewett et al. |
| 4,555,957 A | 12/1985 | Frankel et al. |
| 4,586,546 A | 5/1986 | Mezei et al. |
| 4,621,665 A | 11/1986 | Webb |
| 4,649,116 A | 3/1987 | Daty et al. |
| 4,768,919 A | 9/1988 | Borgman et al. |
| 4,770,454 A | 9/1988 | Muscher et al. |
| 4,837,159 A | 6/1989 | Yamada |
| 4,858,975 A | 8/1989 | Ogawa |
| 4,887,351 A | 12/1989 | Porterfield et al. |
| 4,894,343 A | 1/1990 | Tanaka et al. |
| 4,937,048 A | 6/1990 | Sakai et al. |

(List continued on next page.)

FOREIGN PATENT DOCUMENTS

| WO | WO 97/40383 | 10/1997 | ......... G01N/33/543 |
|---|---|---|---|

OTHER PUBLICATIONS

"Experience The Remarkable Difference . . . with Syringes Designed for Capillary Chromatography," *SGE Solutions*, Issue 2, 1994, p. 1.

"Syringes for Capillary Crhomatography," *SGE Solutions*, Issue 3, 1993, p. 1.

(List continued on next page.)

*Primary Examiner*—Jill Warden
*Assistant Examiner*—Brian R. Gordon
(74) *Attorney, Agent, or Firm*—Brobeck Phlegher & Harrison LLP

(57) ABSTRACT

A system for processing a plurality of solid supports comprises a tubular member having a proximal end, a distal end, and a lumen terminating at the distal end. A stop is positioned within the lumen at a location spaced about the distal end and is sized to permit fluids to pass through the lumen while preventing the passage of solid supports. A fluid transfer device is configured to transfer fluids through the lumen such that when a fluid containing one or more solid supports is aspirated into the lumen, a solid support may be drawn into the lumen to lodge against the stop.

2 Claims, 5 Drawing Sheets

U.S. PATENT DOCUMENTS

| | | | |
|---|---|---|---|
| 4,952,518 A | | 8/1990 | Johnson et al. |
| 4,981,315 A | | 1/1991 | Poli et al. |
| 5,079,170 A | * | 1/1992 | Rosman et al. ............. 436/178 |
| 5,156,811 A | * | 10/1992 | White ........................ 422/100 |
| 5,171,537 A | | 12/1992 | Wainwright et al. |
| 5,185,269 A | | 2/1993 | Wells |
| 5,198,193 A | * | 3/1993 | Bunce et al. ............... 422/100 |
| 5,207,467 A | | 5/1993 | Smith |
| 5,226,462 A | | 7/1993 | Carl |
| 5,280,979 A | | 1/1994 | Poli et al. |
| 5,354,538 A | * | 10/1994 | Bunce et al. ............... 422/100 |
| 5,382,512 A | | 1/1995 | Smethers et al. |
| 5,414,955 A | | 5/1995 | Morin |
| 5,474,744 A | | 12/1995 | Lerch |
| 5,496,523 A | * | 3/1996 | Gazit et al. ................. 422/100 |
| 5,556,598 A | * | 9/1996 | Raybuck et al. .......... 422/10 D |
| 5,567,326 A | | 10/1996 | Ekenberg et al. |
| 5,702,950 A | | 12/1997 | Tajima |
| 5,722,470 A | | 3/1998 | Kedar et al. |
| 5,733,509 A | | 3/1998 | Ackley et al. |
| 5,833,927 A | * | 11/1998 | Raybuck et al. ............ 422/101 |
| 5,849,598 A | | 12/1998 | Wilson et al. |
| 5,851,491 A | * | 12/1998 | Moulton ..................... 422/100 |
| 5,853,894 A | | 12/1998 | Brown |
| 5,916,524 A | * | 6/1999 | Tisone ........................ 422/100 |
| 5,927,547 A | * | 7/1999 | Papen et al. ................ 422/100 |
| 5,935,859 A | | 8/1999 | Elliott et al. |
| 6,045,757 A | * | 4/2000 | Moriarty et al. ............ 422/100 |
| 6,063,339 A | * | 5/2000 | Tisone et al. ................. 422/67 |
| 6,074,609 A | | 6/2000 | Gavin et al. |
| 6,083,762 A | * | 7/2000 | Papen et al. ................ 436/180 |
| 6,096,554 A | * | 8/2000 | Tajima ........................ 436/49 |
| 6,117,394 A | * | 9/2000 | Smith ......................... 422/100 |
| 6,133,037 A | * | 10/2000 | Tajima ........................ 436/49 |
| 6,187,270 B1 | * | 2/2001 | Schmitt et al. ............. 422/101 |
| 6,231,814 B1 | * | 5/2001 | Tajima ........................ 422/101 |
| 2001/0020588 A1 | * | 9/2001 | Adourian et al. ........... 204/451 |

OTHER PUBLICATIONS

"Type B—Do It Yourself Repair Kits," *SGE Analytical Syringes*, Catalogue 1, 1987, p. 1.

"The Ultimate Syringe for Dipensing Microlitre and Sub-microlitre Volumes," *SGE Analytical Syringes*, Catalogue 1, 1987.

Brochure, Labsystems, 384 Technology.

Brochure, Multidrop Dispenser.

Brochure, V&P Scientific, Inc., The Multi–Spense™ 384/96.

Brochure, Robbins, Scientific Corporation, HYDRA™96.

Brochure, Genetix, The New Q Fill2.

Brochure, Matrix Technologies Corporation, Platemate™.

Brochure, Skatron Instruments Inc., Embla 384.

Brochure, Tecan, Genesis Logistics Workstation.

Fischer Scientific Catalog (1988), pp. 884–885, 890.

Normie (Sep./Nov. 1996), article "System uses photonics for early tumor detection," in Biophotonics News, Biophotonics International, pp. 24–25.

Kenichi et al. (1989), "Method for moving spherical carrier for antigen–antibody reaction," Patent Abstracts of Japan, vol. 13, No. 306 (P–897).

* cited by examiner

SYSTEM AND METHOD FOR SINGLE OR MULTIPLE BEAD DISTRIBUTION WITH AN ADJUSTABLE CAPILLARY

BACKGROUND OF THE INVENTION

This invention relates generally to the handling and processing of solid supports, such as beads. More specifically, the invention relates to systems and techniques for placing solid supports into an organized array.

In modem chemistry, large libraries of chemical compounds are often created from which certain compounds which are of interest may be identified. The creation of such libraries may be accomplished with a synthesizing process where various compounds are placed on solid supports, such as spherical beads. Such processes are well known within the art, and are described in, for example, U.S. Pat. No. 5,503,805, the complete disclosure of which is herein incorporated by reference.

After synthesis, it is often desirable to analyze the compounds synthesized on the beads. One such process is by placing an assortment of beads in an assay solution and observing whether a chemical reaction occurs. For example, groups of beads which include synthesized chemicals may initially be placed into a plurality of wells where a portion of the compound on the beads is photo-chemically released. Assays are then performed on each well. For wells producing a positive result, the groups of beads are then transferred into another well or are further divided and placed into a plurality of wells so that further testing can occur to identify the compound. Hence, to successfully perform such assays, the beads need to be transferred to different locations.

When handling such beads, the beads are usually held within a liquid medium, such as water, to help prevent (among other reasons) the beads from sticking together. Usually, such beads are very small, e.g. on the order of about 5 $\mu$m to 300 $\mu$m. As such, transferring of such small beads from one location to another while held within a liquid medium may be difficult and challenging. Transferring such small beads is especially challenging when a known quantity of beads, such as a single bead, must be individually transferred from a group of beads and placed in a test well. Further, it is often convenient to separate the beads into arrays that are compatible with automated screening systems. For example, much of the automated equipment now uses standard footprints, such as 96 well plates, 864 well plates, and the like.

Exemplary techniques for separating and organizing solid supports are described in, for example, U.S. Pat. No. 5,722,470 and U.S. patent application Ser. No. 08/637,123, filed Apr. 24, 1996, the complete disclosures of which are herein incorporated by reference. The invention is related to other techniques for separating solid supports and placing the solid supports into an organized array. The techniques of the invention permit the transferring of a single bead, or a known quantity of beads, in a repeatable manner.

SUMMARY OF THE INVENTION

The invention provides for the transfer of solid supports from one location to another. One particular feature of the invention is the ability to transfer a known quantity of solid supports in a repeatable and efficient manner. In one embodiment, a system for processing a plurality of solid supports comprises a tubular member having a proximal end, a distal end, and a lumen terminating at the distal end. A stop is positioned with the lumen at a location spaced above the distal end and is sized to permit fluids to pass through the lumen while preventing the passage of solid supports. A fluid transfer device is provided to transfer fluids through the lumen such that when a fluid containing multiple solid supports is aspirated into the lumen, one or more solid supports may be drawn into the lumen until lodging against the stop. Hence, a known quantity of solid supports may be captured within the lumen simply by adjusting the position of the stop relative to the distal end of the tubular member. Once the solid supports are captured, the tubular member may be transferred to another location and the solid supports expelled by forcing liquids out of the distal end using the fluid transfer device.

In one particular aspect, the fluid transfer device comprises a syringe pump and a length of tubing coupling the syringe pump to the tubular member. In this way, the syringe pump may be operated to aspirate fluids into the tubular member to capture one or more solid supports into the lumen, and to irrigate fluids from the tubular member to expel any captured solid supports. Conveniently, a source of fluid may be coupled to the syringe pump.

In another particular aspect, the stop comprises a wire that is slidable within the lumen to permit the spacing between the distal end of the wire and the distal end of the tubular member to be adjusted. In this way, the number of potential solid supports that may be captured within a lumen may easily be adjusted.

In still another aspect, a reservoir is provided having a plurality of solid supports. A moving mechanism is also provided to move the tubular member relative to the reservoir to permit placement of the distal end of the tubular member into the reservoir. The system may also include a plate having a plurality of wells, and the moving mechanism may be configured to move the tubular member relative to the plate to permit any solid supports to be expelled from the tubular member and into the wells of the plate. In one particular aspect, the moving mechanism comprises a movable arm to move the tubular member along the Z axis, and a movable stage onto which the reservoir and the plate are held. The stage is movable along the X and Y axes so that the plate may be appropriately positioned relative to the tubular member. Conveniently, a controller may be provided to control operation of the fluid transfer device and the moving mechanism.

Advantageously, the system may include a plurality of tubular members that each have a lumen and a stop disposed within the lumen in a manner similar to that just described. A manifold may be coupled to each of the tubular members, with the fluid transfer device being coupled to the manifold. In this way, the throughput of the system may be greatly increased by introducing the tubular members into an array of reservoirs so that each tubular member may capture one or more solid supports.

In another particular aspect, the lumen may have a diameter in the range from about 190 $\mu$m to about 210 $\mu$m, and the solid supports may have a mean diameter in the range from about 120 $\mu$m to about 140 $\mu$m. Further, the wire may have an outer diameter in the range from about 125 $\mu$m to about 150 $\mu$m to permit fluids to pass between the wire and the tubular member when aspirating and irrigating fluids. However, it will be appreciated that other sizes may be used. For example, in some cases the lumen may have a diameter in the range from about 100 $\mu$m to about 250 $\mu$m.

The invention further provides an exemplary method for processing solid supports having at least one chemical that is synthesized onto the solid supports. According to the method, a tubular member is provided having a proximal end, a distal end, and a lumen terminating at the distal end. A stop is positioned within the lumen at a location spaced above the distal end. The distal end of the tubular member is placed into a fluid having a plurality of solid support, and at least some of the fluid is aspirated into the lumen. The aspirated fluid travels past the stop to draw at least one of the solid supports into the lumen until lodging against the stop. The liquid may be aspirated for a time sufficient to permit the space between the stop and the distal end to be filled with a linear array of solid supports. For example, the tubular member may be employed to capture about one to about 10 solid supports within the lumen, although in some cases larger amounts may be captured.

After the solid supports have been captured within the lumen, the tubular member may be removed from the liquid and transferred to another location. Fluid may then be forced through the lumen and past the stop to expel the solid supports from the tubular member. Conveniently, the fluid and the solid supports may be held within a reservoir, and the tubular member may be moved relative to the reservoir to place the distal end into the fluid. After removing the tubular member from the reservoir, the tubular member may be moved over a multi-well plate to permit the solid supports to be expelled into one of the wells of the plate.

In another aspect, the lumen may be primed with a fluid to remove substantially all gas bubbles from the lumen prior to aspirating the fluid. In another aspect, multiple tubular members may be provided that each have a lumen and a stop within the lumen. In this way, a distal end of each of the tubular members may be simultaneously introduced into the fluid, and fluid aspirated into each of the lumens to draw at least one solid support into each of the lumens.

DESCRIPTION OF THE SPECIFIC EMBODIMENTS

The invention provides techniques for transferring a known quantity of solid supports in a repeatable manner. The techniques may be used to transfer a single solid support or a group of known size. For example, the techniques may be employed to transfer a group that is the range from about 2 to about 10 solid supports in a repeatable manner so that each time a group is transferred, it will contain the same number of solid supports.

In one aspect, the solid supports processed by the invention may comprise small beads onto which chemical compounds have been synthesized. Such beads are typically small, usually being on the order of about 5 $\mu$m to about 300 $\mu$m in diameter, and more usually from about 80 $\mu$m to about 200 $\mu$m. The chemicals may be synthesized onto the solid supports using any one of a variety of techniques as is known in the art, including those described in U.S. Pat. No. 5,503,805, previously incorporated by reference. Such beads may conveniently be constructed of a polymer, such as a polystyrene and polyethylene glycol, and are generally sperical in geometry. Such beads are available from a variety of commercial suppliers, including, for example, Nova Bio-Chem.

One use of the invention is to facilitate screening of the chemical compounds following synthesis. For example, following synthesis, the beads may be placed into one or more common storage locations or reservoirs and stored in a random manner. The invention may be utilized to systematically transfer one or more beads from the reservoir or reservoirs to permit them to be placed into the wells of a multiwell plate where the solid supports may be screened using common screening equipment and techniques. For example, once the beads have been transferred into the wells of the plate, at least some of the compounds may be released from the solid support so that assays may be performed on the released compounds. The assay results may then be measured and certain solid supports may be chosen for decoding in order to identify or further evaluate the compounds. To facilitate this process, the invention may be used to remove the beads from the wells of the multiwell plate for transfer to another location, such as to the wells of another multi-well plate.

The invention facilitates the processing of solid supports with the use of a tubular member having an internal lumen. A stop is placed within the lumen at a location that is spaced apart from the distal end of the tubular member. The stop is configured so that liquids may be aspirated or irrigated through the lumen around the stop. In this way, the tubular member may be placed into a reservoir containing a liquid and solid supports, and liquid aspirated into the lumen until one or more solid supports are drawn into the lumen and engage the stop. The tubular member may then be removed from the reservoir and transferred to another location where a liquid may be forced through the lumen to expel the solid support. Although the invention may utilize a single tubular member, in some cases it may be desirable to include an array or manifold of tubular members to permit the parallel transfer of multiple solid supports or multiple groups of solid supports.

Figure 1:
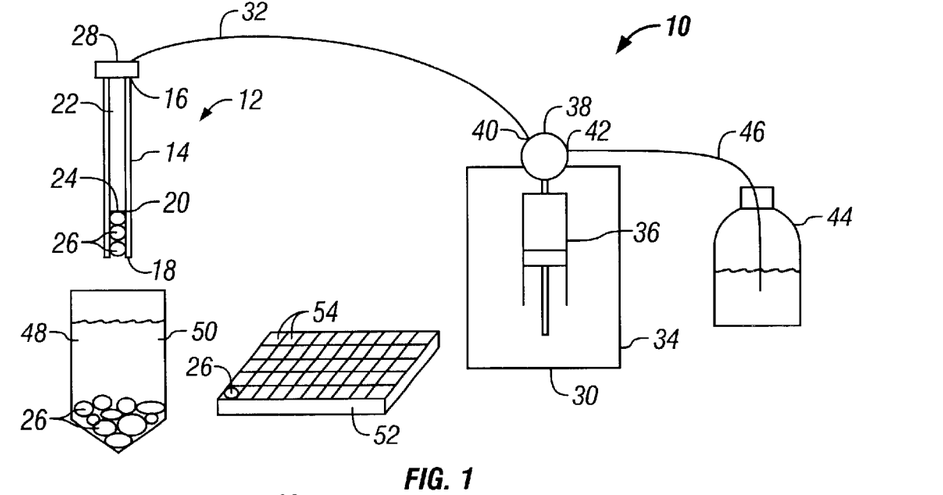
FIG. 1 is a schematic diagram of a system for processing solid supports according to the invention.

Referring now to FIG. 1, a system 10 for processing solid supports will be described. System 10 comprises a capillary tube assembly 12 that is constructed of a capillary tube 14 having a proximal end 16, a distal end 18, and a central lumen 20 extending between proximal end 16 and distal end 18. Conveniently, tube 14 may be constructed of a polyimide tubing, commercially available from Cole-Parmer. Positioned within lumen 20, is a wire 22 having a distal end 24 that is spaced apart from distal end 18 of capillary tube 14. Such a spacing may be varied depending upon the number of beads 26 that are to be captured within lumen 20 as described hereinafter. Wire 22 has an outer diameter that is smaller than the inner diameter of capillary tube 14 to permit liquids to flow through lumen 20 when capturing or expelling the beads.

Coupled to proximal end 16 is a connector 28 to provide a fluid connection between capillary tube 14 and a syringe pump 30 via a line 32. Syringe pump 30 comprises a housing 34 that includes a syringe mechanism 36 and a valve structure 38. Valve structure 38 includes a connector 40 to facilitate coupling of line 32 to syringe pump 30. Valve structure 38 also includes a connector 42 to permit a liquid supply 44 to be coupled to syringe pump 30 via a line 46. Valve structure 38 is configured so that when syringe mechanism 36 is extended, liquid from supply 44 is drawn through line 46 and into syringe mechanism 36. When syringe mechanism 36 is compressed, the captured liquid is forced out of connector 40 and through line 32 where it flows through capillary tube 14. One example of such a syringe pump that is configured to operate in this manner is a XL 3000 Modular Digital syringe pump, commercially available from Cavro Scientific Instruments, Inc. However, it will be appreciated that other types of syringe pumps, as well as other types of fluid transfer systems may be employed to irrigate liquids through lumen 20 as well as to aspirate fluids into lumen 20.

System 10 further includes a reservoir 48 containing a supply of beads 26 which are held within a liquid 50. Beads 26 are generally spherical in geometry and may include synthesized chemicals that form a combinatorial library of chemical compounds as previously described. The types of liquid in which beads 26 may be stored include liquids such as water, 50% ethanol in water, and the like. Typically, the liquid within supply 44 will comprise the same type of liquid held in reservoir 48. System 10 also includes a plate 52 having a plurality of wells 54 for receiving one or more beads that have been transferred from reservoir 48. Conveniently, plate 52 may be constructed to have a standard footprint so that it may be useful with standardized equipment when screening the chemical compounds, as well as for other processes as is known in the art.

In one method of operation, beads are transferred from reservoir 48 to wells 54 by first operating syringe pump 30 to fill syringe mechanism 36 with liquid from supply 44. In this way, line 56 is completely filled with liquid. Syringe pump 30 is then operated to force liquid through line 32, thereby priming line 32 and filling lumen 20. Preferably, syringe pump 30 is operated until lumen 20 is substantially completely filled with liquid to remove any gas bubbles. Capillary tube 14 may then be inserted into reservoir 48 and syringe pump 30 may again be operated to irrigate a small amount of fluid through lumen 20 to ensure that no gas bubbles exist within lumen 20 as well as to compensate for the amount of liquid that will be lost when beads 26 are aspirated into capillary tube 14. In some cases, the released liquid may also serve to provide a small stirring effect on beads 26 to facilitate their capture into lumen 20.

Syringe pump 30 is then operated to aspirate liquids into lumen 20. As liquid from reservoir 48 is aspirated into lumen 20, some of beads 26 are drawn into lumen 20 as shown. The number of beads that may be captured into lumen 20 depends on the distance between distal end 24 of wire 22 and distal end 18 of capillary tube 14. As shown, three beads have been captured in a linear array. However, it will be appreciated that other numbers of beads may be captured during a single picking operation. For example, wire 22 may be configured so that only a single bead is captured during each picking step. Alternatively, groups from about two to about 10 beads may be captured at a time. Configuration of capillary tube assembly 12 is advantageous in that a known quantity of beads may be captured each time a picking operation is performed. In this way, a known quantity of beads may be captured and transferred in a repeatable and efficient manner.

Syringe pump 30 is operated for a time sufficient to allow the beads to be captured within lumen 20. After a certain time period, operation of syringe pump 30 is ceased and capillary tube 14 is removed from reservoir 48. Capillary tube assembly 12 is then moved over plate 52 until capillary tube 14 is aligned with a desired well 54. Syringe pump 30 is then operated to force liquid through line 32 to expel the captured beads into the aligned well. Capillary tube assembly 12 may then be moved over reservoir 48 and the process repeated to transfer beads 26 into the desired number of wells. Plate 52 is then ready for appropriate biological screening or other processing as is known in the art.

Figure 2:
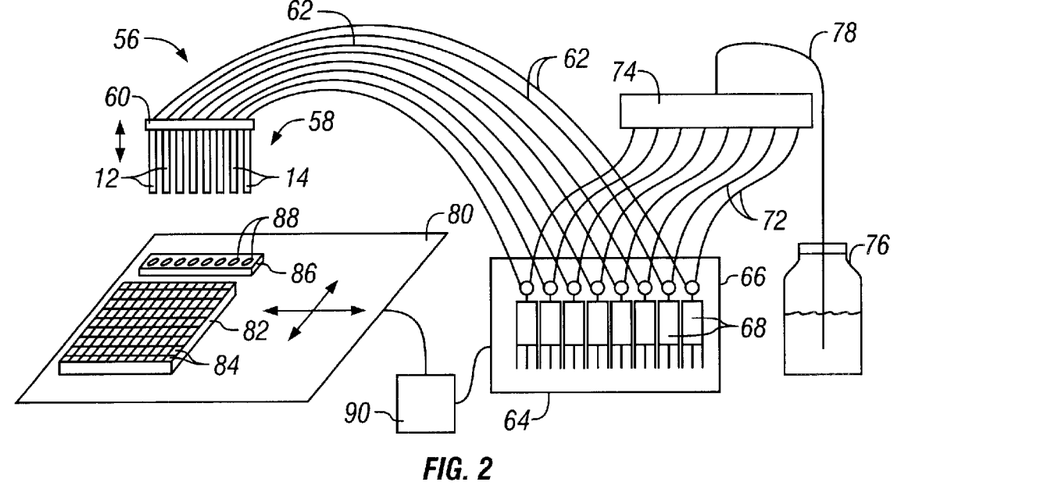
FIG. 2 is a schematic. diagram of an alternative system for processing solid supports according to the invention.

In some cases, it may be desirable to increase the number of capillary tubes in order to increase the number of beads that may be transferred during a single picking operation. One system 56 that includes such features is illustrated in FIG. 2. System 56 comprises a capillary tube manifold assembly 58 which includes an array of capillary tube assemblies that may be constructed in a manner similar to that previously described in connection with FIG. 1. Hence, for convenience of discussion, the capillary tube assemblies will be described using the same reference numerals used in describing capillary tube assembly 12 of FIG. 1. For convenience of illustration, capillary tube manifold assembly 58 is shown in greater detail in FIG. 3.

Figure 3:
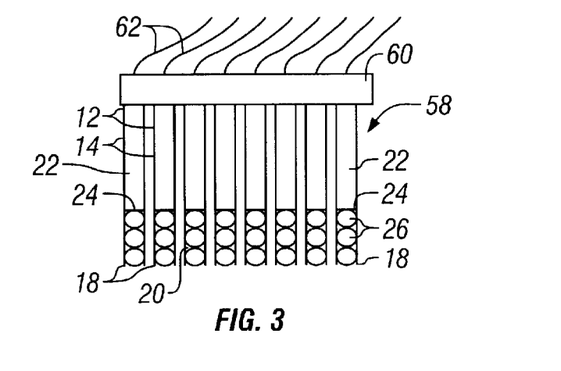
FIG. 3 is a more detailed view of an array of tubular members employed to capture and transfer solid supports.

Fluidly connecting each capillary tube assembly 12 is a fluid manifold 60. As shown, assembly 58 includes eight capillary tubes 14. Further, eight fluid delivery lines 62 are coupled to manifold 60. Fluid lines 62 are in turn coupled to a syringe pump 64. However, it will appreciated that other numbers of capillary tubes may be incorporated into manifold assembly 58. Further, although a separate fluid delivery line is provided for each capillary tube 14, it will be appreciated that manifold 60 may be configured to evenly distribute fluids or provide suction to each capillary tube 14 so that only one fluid delivery line would be needed. In such a case, syringe pump 64 may be configured to be essentially identical to syringe pump 30 of FIG. 1.

Syringe pump 64 comprises a housing 66 that includes multiple syringe mechanisms 68 that may be similar to syringe mechanism 36 of FIG. 1. Valve structures 70 are also provided to permit coupling of syringe mechanism 68 to fluid delivery lines 62. Also coupled to valve structure 70 are fluid delivery lines 72 that terminate at a manifold 74 which receives liquid from a liquid supply 76 via a line 78.

With such a configuration, syringe pump 64 may be operated to fill syringe mechanism 68 with liquid from supply 76. Syringe pump 64 may then be operated to prime lines 62 and to aspirate liquids into capillary tubes 14 to capture beads within capillary tubes 14 in a manner similar to that previously described in connection with FIG. 1.

System 56 further includes a movable stage 80 which is movable along X and Y axes as indicated by the arrows. Positioned on stage 80 is a multi-well plate 82 having a plurality of wells 84 as is known in the art. Also held on stage 80 is a plate 86 having a plurality of reservoirs 88 that each include multiple solid supports. Conveniently, reservoirs 88 may include beads which originated from the same or from a different synthesis pool/library. Use of reservoirs 88 is advantageous in that the beads may be stored within plate 86 without experiencing cross-contamination. Although not shown, a mechanism is also provided to translate manifold assembly 58 along the Z axis to permit capillary tubes 12 to be moved into reservoirs 88 and into wells 84 as described hereinafter. Conveniently, a controller 90 is provided to control movement of stage 80, movement of the mechanism to move manifold assembly 50 and to control operation of syringe pump 64. In this way, the transfer of beads may occur in a fully automated manner.

For example, one method of operation for transferring beads from reservoirs 88 to wells 84 is by using controller 90 to operate syringe pump 64 to fill syringe mechanisms 68 with liquid from supply 76 as previously described. Controller 90 may then send a signal to syringe pump 64 to prime lines 62 and lumens 20. Controller 90 may then send a signal to stage 80 to align reservoirs 88 with capillary tubes 14 and to move manifold assembly 58 downward until capillary tubes 14 are within reservoirs 88.

Once capillary tubes 14 are within reservoirs 88, controller 90 may be operated to further prime the lines and to expel any liquid in order to compensate for the liquid to be aspirated when sucking the beads within capillary tubes 14. Controller 90 then sends a signal to syringe pump 64 to aspirate liquids into capillary tubes 14 for a time sufficient to capture the desired number of beads into each of capillary tubes 14. As with system 10 of FIG. 1, the number of captured beads may be controlled simply by controlling the length of wire 22 within lumen 20. After the specified time has elapsed, controller 90 sends a signal to remove capillary tubes 14 from reservoirs 88. Stage 80 is then moved to align capillary tubes 14 with a desired row of wells in plate 82. Manifold assembly 58 is then moved downward and controller 90 sends a signal to syringe pump 64 to irrigate liquids through capillary tubes 14 in order to expel the captured beads into the aligned wells 84 of plate 82. This process may be repeated as many times as desired in order to fill each of wells 84 of plate 82. Plate 82 may then be used in a biological screening or other process as is known in the art.

System 56 may also be used to transfer beads from one multiwell plate to another. For example, if one of wells 84 produced a positive result during the screening process, system 56 may be employed to individually remove the beads from that well and to place them into the wells of another multiwell plate so that further screening may occur to identify the compound synthesized onto the bead.

Figure 4:
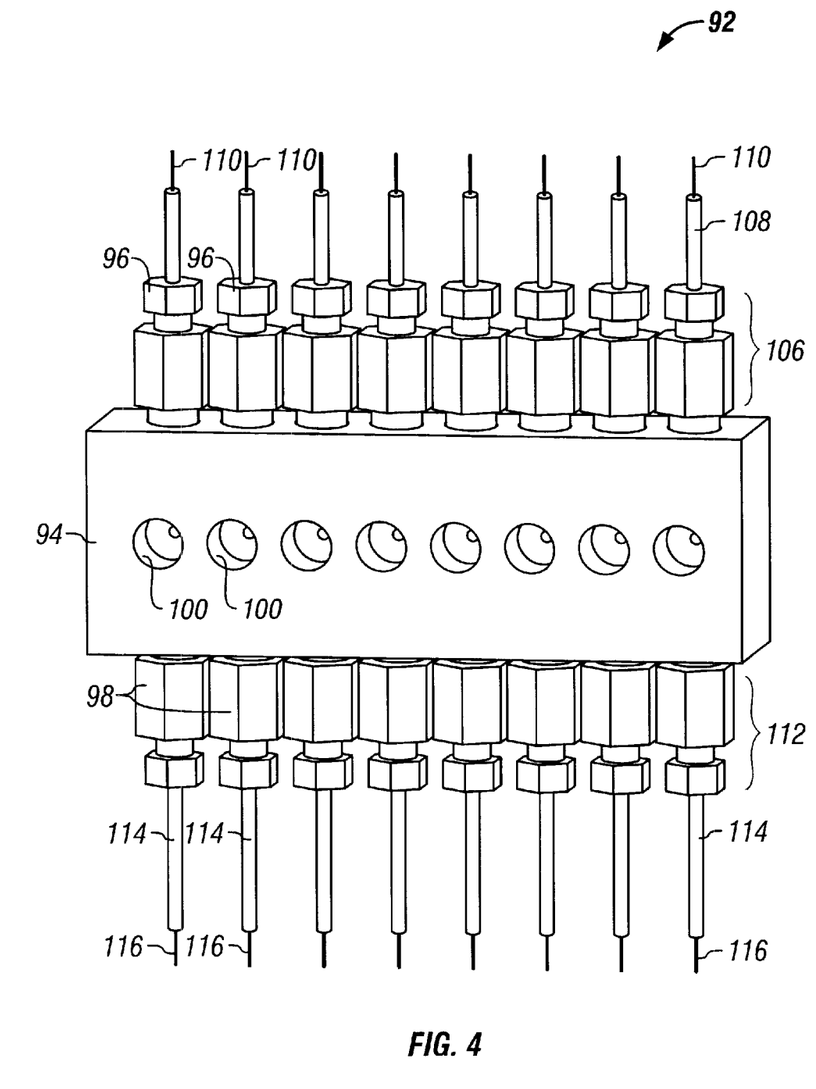
FIG. 4 is a front perspective view of one exemplary embodiment of a multichannel capillary manifold that may be employed to simultaneously process multiple solid supports according to the invention.
Figure 5:
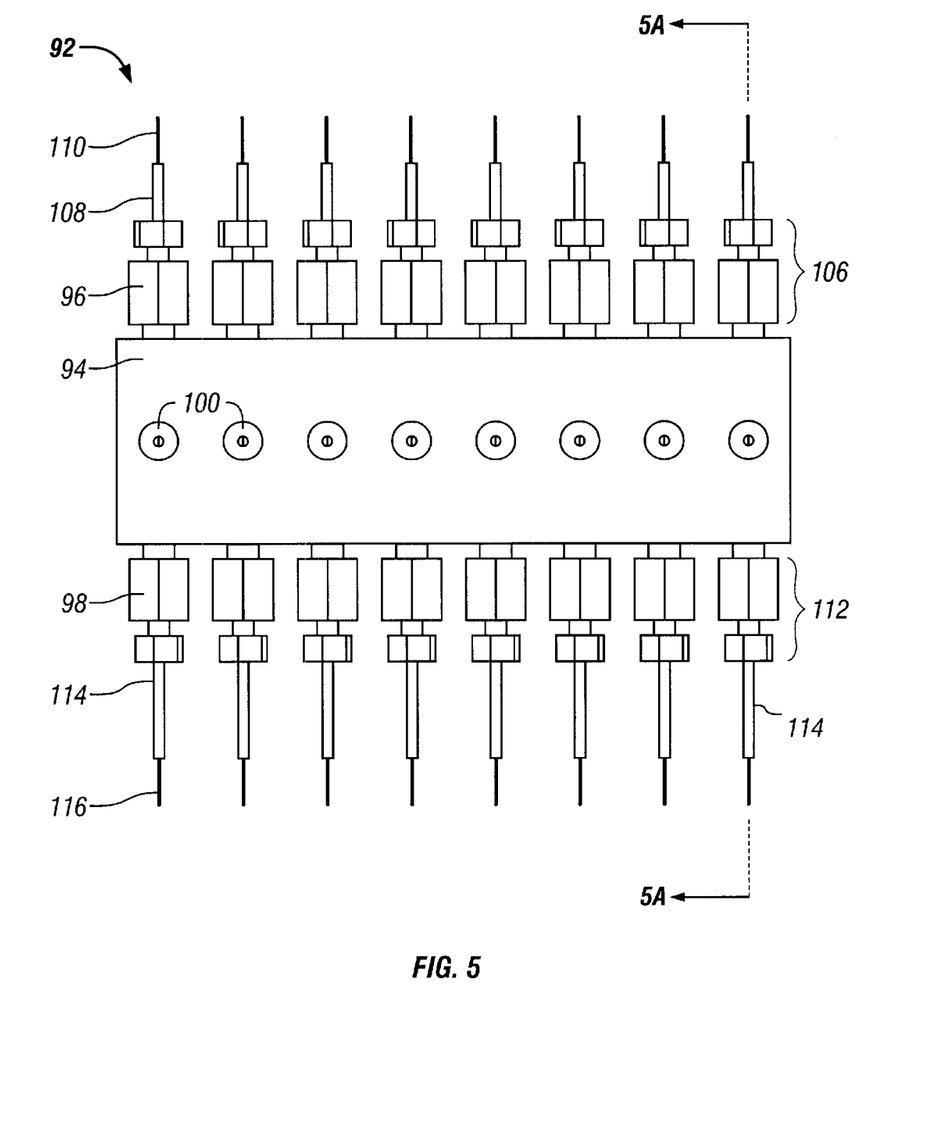
FIG. 5 is a front view of the manifold of FIG. 4.

Referring now to FIGS. 4 and 5, one embodiment of a capillary tube of manifold assembly 92 will be described. Assembly 92 comprises a housing 94 to which are coupled a plurality of wire adjustment mechanisms 96 and a plurality of capillary tube assemblies 98. Housing 94 includes a plurality of ports 100 to permit manifold assembly 92 to be coupled to a syringe pump in a manner similar to that described with previous embodiments. As best shown in FIG. 6, housing 94 further includes a plurality of openings 102 into which wire adjustment mechanisms 96 may be inserted. Housing 94 further includes openings 104 for receiving capillary tube assemblies 98.

Figure 5A:
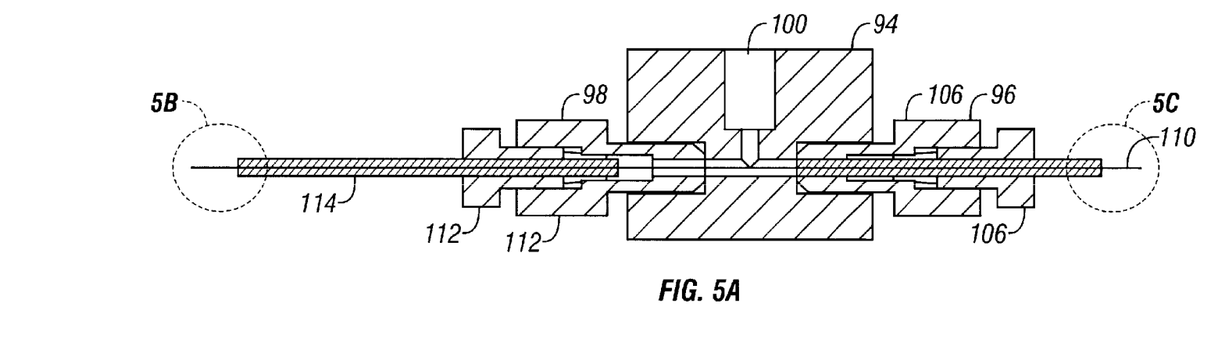
FIG. 5A is a cross-sectional side view of the manifold of FIG. 5 taken along lines A—A.
Figures 5B, 5C, 6:
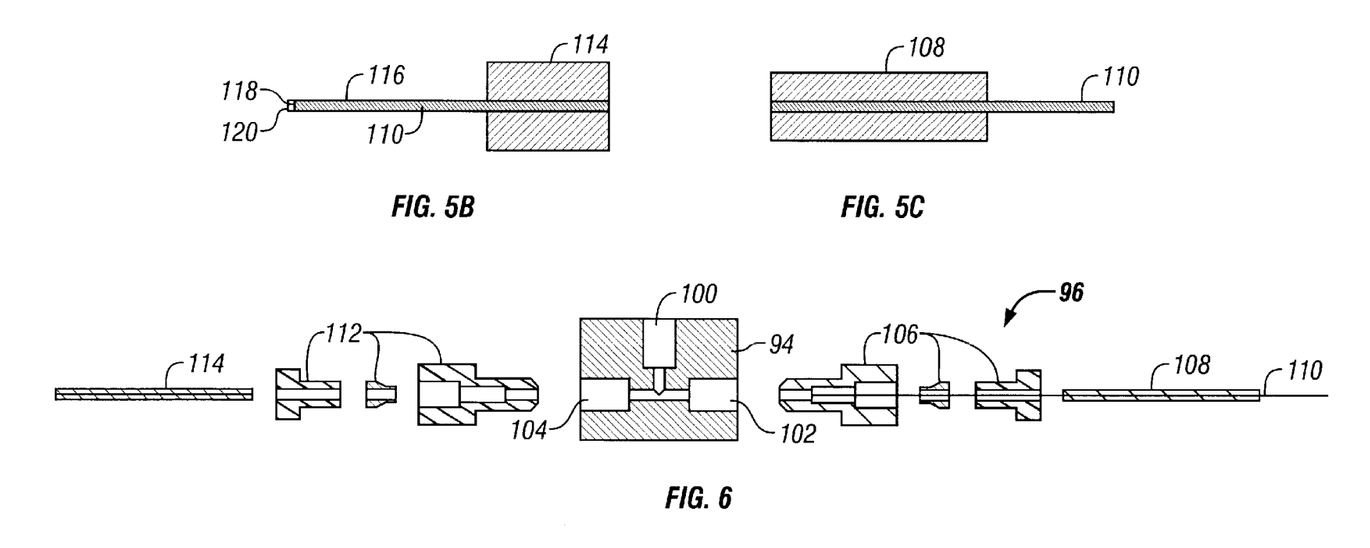
FIG. 5B is a more detailed view of a tubular member of section B of the manifold of FIG. 5A.
FIG. 5C is a more detailed view of a wire of section C of FIG. 5A.
FIG. 6 is an exploded view of the capillary manifold of FIG. 5A.

As best shown in FIGS. 5A and 6, wire adjustment mechanism 96 comprises a female/male adapter 106 that is insertable into opening 102. Insertable into adapter 106 is a sleeve 108 through which a wire 110 is inserted. Merely by way of example, female/male adapted 106 may be constructed of a stainless steel 10-32 to 114-28 adapter, commercially available from Upchurch Scientific. Sleeve 108 may be constructed of a PEEK tubing sleeve, 0.008 inch OD, 1.25 inch long, commercially available from Upchurch Scientific. Wire 110 may be obtained from California Fine Wire Company. Positioning of wire 110 through sleeve 108 is shown in greater detail in FIG. 5C. Sleeve 108 is configured such that wire 110 may slide through sleeve 108 to adjust the distance with which wire 110 extends into capillary tube assembly 98. The connection between sleeve 108 and wire 110 is also configured to provide a sufficient seal so that liquids introduced into or withdrawn from port 100 will not leak through sleeve 108. Further, the connection between sleeve 108 and adaptor 106 are configured to prevent any fluid leakage.

Capillary tube assembly 98 comprises a female/male adaptor 112 that is insertable into opening 104 of housing 94. Adaptor 112 is employed to couple a sleeve 114 to housing 94. Inserted into sleeve 114 is a length of tubing 116. Movably received within tubing 116 is wire 110.

Hence, by grasping wire 110 where it exits sleeve 108, a user may adjust the distance between a distal end 118 of wire 10 and a distal end 120 of tubing 116. This distance, in turn, defines a space where the beads will be captured. Hence, the number of beads that may be captured into tubing 116 may be adjusted simply by adjusting the location of wire 110 within tubing 116. Conveniently, the adjustment of wire 110 may occur manually or with the use of automated equipment.

The connection between sleeve 114 and tubing 116, as well as the connection between sleeve 114 and adapter 112, are sufficiently tight to prevent any fluid leakage. However, the spacing between wire 110 and tubing 116 is sufficient to permit the passage of fluids, such as when providing a vacuum for the bead picking process or positive pressure for fluid delivery or bead dispensing.

It will be appreciated that manifold assembly 92 may be constructed of a variety of material and to have a variety of sizes. Merely by way of example, housing 94 may be constructed of polypropylene, stainless steel, Teflon, or the like. Tubing 116 may be constructed of a polyimide capillary tube and may have, for example, a 198 $\mu$m inner diameter and a 236 $\mu$m outer diameter. Wire 110 may be constructed of tungsten and have a diameter of about 127 $\mu$m. Such dimensions are particularly useful with beads having a diameter in the range from about 120 $\mu$m to about 140 $\mu$m. However, it will be appreciated that the dimensions of manifold assembly 92 may be varied depending on the particular size of bead, the fluids involved, and the like.

Hence, in a bead picking operation, length of tubing 116 may be inserted into reservoirs having a plurality of beads. Fluids may then be aspirated through port 100 which causes a suction force to be created at distal end 112 of tubing 116. As such, one or more beads will be drawn into tubing 16 depending upon the positioning of wire 110 within tubing 116. Once the beads have been captured, manifold assembly 92 may be moved to another location and fluid under positive pressure introduced into port 110 to cause fluid to be irrigated out of tubing 116 to expel the captured beads.

Figure 7:
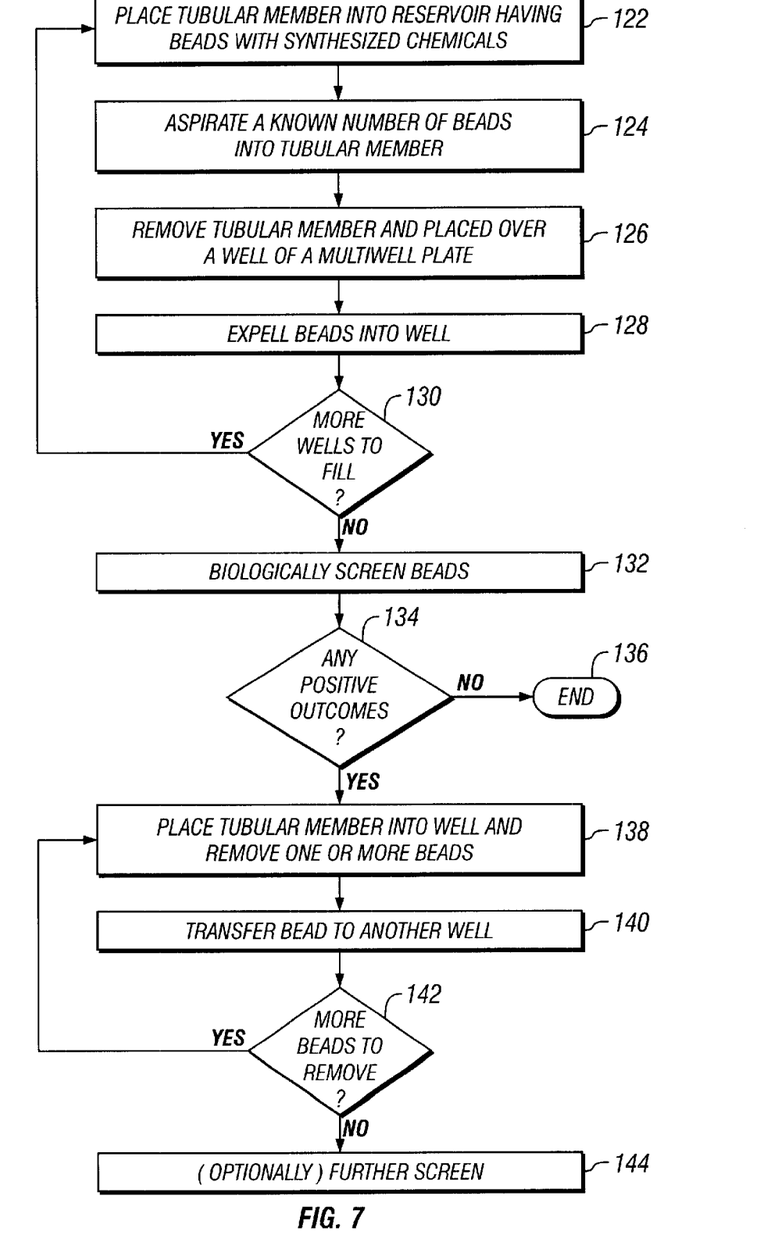
FIG. 7 is a flow chart illustrating one method for processing solid supports according to the invention.

Referring now to FIG. 7, one method for transferring beads as part of a biological screening process will be described. The process begins at step 122 where tubular member is placed into a reservoir having beads with the synthesized chemicals. A known number of beads is then aspirated into the tubular member as illustrated in step 124. The tubular member is then removed from the reservoir and placed over a well of a multiwell plate as shown in step 126. Positive pressure is introduced into the tubular member to expel the beads into one of the wells as illustrated in step 128. If more wells are to receive beads, the process reverts back to step 122 as illustrated in step 130. If all of the desired wells are filled with beads, the process proceeds to step 132 where the beads within the wells may be biologically screened according to processes known in the art. The wells are then evaluated for any positive outcomes as illustrated in step 134. If no positive outcomes are identified, the process ends at step 136. If one or more wells are identified, the process proceeds to step 138 and the tubular member may be introduced into the well to remove one or more of the beads. The bead may then be transferred to another well as illustrated in step 140. This process is repeated as many times as necessary in order to remove all of the beads as illustrated in step 142. Optionally, as shown in step 144, the transferred beads may be further screened as shown in step 144 to identify the compounds on the beads.

The invention has now been described in detail for purposes of clarity of understanding. However, it will be appreciated that certain changes and modifications may be practiced within the scope of the appended claims.

What is claimed is:

1. A device for processing solid supports that are held within a fluid, the device comprising:

a tubular member having a proximal end, a distal end, and a lumen terminating at the distal end, wherein the lumen has a diameter in the range from about 190 μm to about 210 μm;

a wire positioned within the lumen at a location spaced above the distal end, wherein the wire has an outer diameter in the range from about 125 μm to about 150 μm to permit fluids to pass through the lumen while preventing passage of solid supports when fluids are aspirated into the lumen from the distal end.

2. A system for processing a plurality of solid supports, the system comprising:

a tubular member having a proximal end, a distal end, and a lumen terminating at the distal end;

a stop positioned within the lumen at a location spaced above the distal end, wherein the stop is sized to permit fluids to pass around the stop through the lumen while preventing passage of solid supports, said stop comprising a wire that is slidable within the lumen to permit the spacing between a distal end of the wire and the distal end of the tubular member to be adjustable; and a fluid transfer device that is configured to transfer fluids through the lumen such that when a fluid containing one or more solid supports is aspirated into the lumen, a solid support may be drawn into the lumen to lodge against the stop.

* * * * *